United States Patent [19]

Connor et al.

[11] Patent Number: 5,338,487

[45] Date of Patent: Aug. 16, 1994

[54] CATALYZED PROCESS FOR GLUCAMIDE DETERGENTS

[75] Inventors: Daniel S, Connor; Jeffrey J. Scheibel; Ju-Nan Kao, all of Cincinnati, Ohio

[73] Assignee: The Procter & Gamble Company, Cincinnati, Ohio

[21] Appl. No.: 9,369

[22] Filed: Jan. 26, 1993

Related U.S. Application Data

[63] Continuation of Ser. No. 590,639, Sep. 28, 1990, abandoned.

[51] Int. Cl.$^5$ .............. B01F 17/22; C07C 233/01; C11D 7/32
[52] U.S. Cl. .................... 252/357; 252/548; 554/66
[58] Field of Search ............ 252/357, 548; 554/35, 554/66, 69, 68

[56] References Cited

U.S. PATENT DOCUMENTS

| | | | |
|---|---|---|---|
| 1,985,424 | 12/1934 | Piggott | 260/124 |
| 2,016,962 | 10/1935 | Flint et al. | 260/127 |
| 2,356,565 | 8/1944 | Chwala | 252/357 X |
| 2,653,932 | 9/1955 | Schwartz | 260/211 |
| 2,662,073 | 12/1953 | Mehltretter et al. | 260/102 |
| 2,667,478 | 1/1954 | Schwartz | 252/548 X |
| 2,703,798 | 3/1955 | Schwartz | 260/211 |
| 2,844,609 | 7/1958 | Tesoro | 260/404 |
| 2,891,052 | 6/1959 | Boettner et al. | 260/211 |
| 2,921,909 | 1/1960 | Osipow et al. | 252/548 X |
| 2,954,347 | 9/1960 | St. John et al. | 252/109 |
| 2,991,296 | 7/1961 | Scherr | 260/404 |
| 2,993,887 | 7/1961 | Zech | 260/211 |
| 3,257,436 | 6/1966 | Lindner | 260/404 |
| 3,285,856 | 11/1966 | Lew | 252/152 |
| 3,576,749 | 4/1971 | Megson et al. | 252/132 |
| 3,637,495 | 1/1972 | Eckert et al. | 252/8.8 |
| 3,654,166 | 4/1972 | Eckert et al. | 252/548 X |
| 3,704,228 | 11/1972 | Eckert | 252/117 |
| 3,920,586 | 11/1975 | Bonaparte et al. | 252/531 |
| 3,929,678 | 12/1975 | Laughlin et al. | 252/526 |
| 3,985,669 | 10/1976 | Krummel et al. | 252/116 |
| 3,988,255 | 10/1976 | Seiden | 252/107 |
| 4,094,808 | 6/1978 | Stewart et al. | 252/186 |
| 4,129,511 | 12/1978 | Ogoshi et al. | 252/140 |
| 4,223,163 | 9/1980 | Guilloty | 568/618 |
| 4,292,212 | 9/1981 | Melby | 252/547 |
| 4,483,781 | 11/1984 | Hartman | 252/174.12 |
| 4,540,821 | 9/1985 | Larkin et al. | 564/473 |
| 4,565,647 | 1/1986 | Llenado | 252/354 |
| 4,664,839 | 5/1987 | Rieck | 252/175 |
| 4,704,224 | 11/1987 | Saud | 252/132 |
| 4,843,154 | 6/1989 | Klein et al. | 536/4.1 |
| 5,009,814 | 4/1923 | Kelkenberg et al. | 252/528 |
| 5,188,769 | 2/1993 | Conner et al. | 252/548 |
| 5,283,009 | 2/1994 | Speckman et al. | 252/548 |
| 5,298,636 | 3/1994 | Conner et al. | 554/66 |

FOREIGN PATENT DOCUMENTS 206283 2/1957 Australia .

(List continued on next page.)

OTHER PUBLICATIONS

Synthesis of Long Chain N-Alkyllactylamines from Unprotected Lactose-A new Series of Non-Ionic Surfactants, Latge et al. J. Dispersion Science and Technology, 12(3&4), pp. 227–237 (1991).

U.S. patent application Ser. No. 07/755,900, filed Sep. 6, 1991 (Ofosu-Asante et al) entitled Detergent Compositions Containing Calcium and Polyhydroxy Fatty Acid Amide (not enclosed).

(List continued on next page.)

*Primary Examiner*—Robert L. Stoll
*Assistant Examiner*—Daniel S. Metzmaier
*Attorney, Agent, or Firm*—Jerry J. Yetter; George W. Allen

[57] ABSTRACT

An improved process for manufacturing a linear glucamide surfactant comprises reacting an N-alkylglucamine, e.g., N-methylglucamine, a fatty ester, e.g., coconut methyl ester and a catalyst selected from trilithium phosphate, trisodium phosphate, tripotassium phosphate, tetrasodium pyrophosphate, tetrapotassium pyrophosphate, pentasodium tripolyphosphate, pentapotassium tripolyphosphate, lithium hydroxide, sodium hydroxide, potassium hydroxide, calcium hydroxide, lithium carbonate, sodium carbonate, potassium carbonate, disodium tartrate, dipotassium tartrate, sodium potassium tartrate, trisodium citrate, tripotassium citrate, sodium basic silicates, potassium basic silicates, sodium basic aluminosilicates, potassium basic aluminosilicates and mixtures thereof.

3 Claims, No Drawings

FOREIGN PATENT DOCUMENTS

| | | |
|---|---|---|
| 220676 | 5/1987 | European Pat. Off. ... C07C 103/38 |
| 255033 | 7/1987 | European Pat. Off. ........ C07H 1/04 |
| 282816 | 9/1988 | European Pat. Off. ........ A61K 7/48 |
| 0285768 | 12/1988 | European Pat. Off. ........ C11D 3/32 |
| 422508 | 4/1991 | European Pat. Off. ........ A61K 7/06 |
| 53839 | 2/1967 | Fed. Rep. of Germany . |
| 2038103 | 2/1972 | Fed. Rep. of Germany . |
| 2226872 | 12/1973 | Fed. Rep. of Germany ......... C11D 03/32 |
| 2226872 | 12/1973 | Fed. Rep. of Germany ......... C11D 03/32 |
| 1580491 | 9/1969 | France . |
| 2657611 | 2/1991 | France .......................... C07H 5/06 |
| 2657611 | 2/1991 | France .......................... C07H 5/06 |
| 8304412 | 12/1983 | PCT Int'l Appl. ........ C07C 103/38 |
| 420518 | 11/1934 | United Kingdom . |
| 519381 | 3/1940 | United Kingdom . |
| 771423 | 4/1957 | United Kingdom . |
| 809060 | 2/1959 | United Kingdom . |
| 2242686 | 9/1991 | United Kingdom ........ C11D 1/722 |

OTHER PUBLICATIONS

"N–D–Gluco–N–methylalkanamide Compounds, a New Class of Non–Ionic Detergents For Membrane Biochemistry", Biochem. J. (1982) vol. 207, pp. 363–366, Hildreth H. Kelkenberg, Tenside Surfactants Detergents 25 (1988) pp. 8–13.

Relative Stabilities of d–Glucose–Amine Derivatives, Mohammad and Olcott, JACS, Apr. 1947, p. 969.

[23] 1–Amino–1–deoxy–D–glucitol, Long and Bollenback, Meth. Carbohyd. Chem., vol. 2, (1963), pp. 79–83.

The Reaction of Glucose with Some Amines, Mitts and Hixon, JACS, vol. 66, (1944), pp. 483–486.

Synthesis of $^{14}$C–Labeled N–Methylglucamine, Heeg et al, Can. J. of Pharmaceutical Sciences, vol. 10, No. 3 (1975), pp. 75–76.

Derwent Abstract, 91–183/88 (Corresponding to JO3112904 91.05.14).

Chemical Abstracts, CA 84(2):8854M (Corresponding to DE2404070).

CATALYZED PROCESS FOR GLUCAMIDE DETERGENTS

This is a continuation of application Ser. No. 07/590,639, filed on Sep. 28, 1990 now abandoned.

TECHNICAL FIELD

This invention is in the detergent field and relates to improved processes for condensing N-alkylglucamines with fatty esters in the presence of certain catalysts to produce laundry detergent surfactants.

BACKGROUND OF THE INVENTION

The present invention is set against a background of change in society's attitudes to how natural resources are used. Petroleum feedstocks are non-renewable and increasingly costly, even impacting significantly on national balances of payment, and supply can be uncertain. There is a perception, increasingly commonly held, that it may be for the general good of society, as well as of the environment, to reduce the reliance of consumer disposable goods manufacturing on such feedstocks. However, a serious response to such notions requires efficient processes for converting locally or regionally available renewable resource feedstocks into desirable consumer goods such as laundry detergents.

The United States produces very considerable tonnages of sugars, such as glucose or corn syrup, as well as of fatty substances. There is a downward trend in traditional patterns of consumption of these particular renewable resources: people are tending to eat less sugars, and also less fatty foods, especially saturated fats, for health-related reasons. This makes their development for other uses, such as laundry detergents, all the more attractive.

A number of years ago, processes were explored for making textile assistants or detergents from fatty acids or their derivatives in combination with N-alkylglucamines, the latter made by reductive amination of glucose. Glucose reductive amination processes are more fully disclosed in U.S. Pat. No. 2,016,962, Flint et al, issued Oct. 8, 1935.

U.S. Pat. No. 1,985,424, Piggott, issued Dec. 25, 1934, discloses manufacturing "textile assistants" by reacting (a) the product of heating glucose and aqueous methylamine in presence of hydrogen and a hydrogenating catalyst under pressure with (b) an organic carboxylic acid such as stearic acid or oleic acid. The condensation product, prepared at about 160° C., is said to be "predominantly, if not exclusively, an amide" and is assertedly of the formula R—CO—NR$_1$—CH$_2$—(CHOH)$_4$—CH$_2$OH wherein R is an alkyl radical containing at least 3 carbon atoms, while R$_1$ is hydrogen or an alkyl radical.

U.S. Pat. No. 2,703,798, Schwartz, issued Mar. 8, 1955, asserts that compositions produced by reacting fatty acids or acid anhydrides with N-alkylglucamines (presumably such as the process as taught by Piggott) have poor color and poor detergency properties. It is indeed chemically reasonable that more than one compound can be formed by the Piggott process. Piggott makes no attempt to quantitatively prove the structures of the compounds or mixtures he prepared.

Schwartz ('798) goes on to report an improvement as a result of reacting fatty ester (as distinct from fatty acid or anhydride) with N-alkylglucamines. Although this process may overcome one or another deficiency of the art, such as of Piggott, it now transpires that the Schwartz process still has difficulties, in particular, in that complex mixtures of compounds can be formed even by the Schwartz process. The reaction may take several hours and the process can fail to give high quality product. Neither the process of Piggott not the process of Schwartz is known to have ever borne fruit in commercial practice.

In more detail, Schwartz notes that only one of several possible chemical reactions takes place when N-monoalkylglucamines are condensed with fatty esters or oils. The reaction is said to give compounds formulated as amides, e.g.,

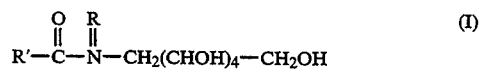

where R' is fatty alkyl and R is a short-chain alkyl, typically methyl. This structure is apparently the same as the structure proposed by Piggott. Schwartz contrasts the single-product outcome he believes he secures with compounds he asserts are actually produced when acids are reacted with N-alkylglucamines, namely mixtures of the amide (I) with one or more by-products, to which he assigns esteramide and esteramine structures and which assertedly include compounds which are "inert and waxy, impairing the surface activity of" the structure (I) amide.

According to Schwartz, approximately equimolar proportions of N-monoalkylglucamines can be reacted with fatty alkyl esters by heating at 140° C.–230° C., preferably 160° C.–180° C. at normal, reduced or superatmospheric pressures for a period "somewhat in excess of one hour" during which time two initially immiscible phases merge to form a product said to be a useful detergent.

Suitable N-monoalkylglucamines are illustrated by N-methylglucamine, N-ethylglucamine, N-isopropylglucamine and N-butylglucamine. Suitable fatty alkyl esters are illustrated by the product of reacting a C$_6$–C$_{30}$ fatty acid with an aliphatic alcohol e.g., methyl ester of lauric acid. Mixed glycerides of Manila oil or mixed glycerides of cochin coconut oil can apparently also be used as the fatty ester. When the glucamine is N-methylglucamine, the corresponding products with these fatty esters are characterized as the "fatty acid amides of N-methylglucamine", which are useful detergent surfactants. Another specific composition reported is assertedly "N-isopropylglucamine coconut fatty acid amide".

U.S. Pat. No. 2,993,887, Zech, issued Jul. 25, 1961, reveals there is even more complexity to the reactions of fatty substances with N-methylglucamine. In particular, Zech asserts that the products of high-temperature reaction (180° C.–200° C.) within the range disclosed by Schwartz have cyclic structures. No fewer than four possible structures are given. See '887 at col. 1 line 63–col. 2 line 31.

What is now believed actually to be provided by the fatty ester- N-alkylglucamine process of Schwartz are compositions comprising mixtures of formula (I) compounds together with appreciable proportions (e.g., about 25%, often much more) of several other components, especially cyclic glucamide by-products (including but not limited to the structures proposed by Zech) or related derivatives such as esteramides wherein as compared with formula (I) at least one —OH moiety is esterified.

Moreover, a reinvestigation of Schwartz suggests that there are other significant unsolved problems in the process, including a tendency to form trace materials imparting very unsatisfactory color and/or odor to the product.

More recently, the work of Schwartz notwithstanding, Hildreth has asserted that compounds of formula (I) are new. See Biochem. J., 1982, Vol. 207, pages 363–366. In any event, these compositions are given a new name: "N-D-gluco-N-methylalkanamide detergents", and the acronym "MEGA". Hildreth provides a solvent-assisted process for making the compounds differing seminally from Schwartz in that it returns to the use of a fatty acid reactant, instead of fatty ester. Moreover, Hildreth relies on pyridine/ethyl chloroformate as the solvent/activator. This process is specifically illustrated for octanoyl-N-methylglucamide ("OMEGA"), nonanoyl-N-methylglucamide ("MEGA-9") and decanoyl-N-methylglucamide ("MEGA-10"). The process is said to be cheap and high-yield. One must of course assume that "cheap" is relative and is meant in the sense of specialized biochemical applications of interest to the author: in terms of large-scale detergent manufacture, the use of pyridine and ethyl chloroformate would hardly be viewed as consistent with an economic or environmentally attractive process. Therefore, the Hildreth process is not further considered herein.

Hildreth and other workers have purified certain formula (I) compounds, e.g., by recrystallization, and have described the properties of some of the structure (I) compounds. Recrystallization is, of course, a costly and potentially hazardous (flammable solvents) step in itself, and large-scale detergent manufacture would be more economical and safer without it.

According to Schwartz supra, the products of the Schwartz process can be used for cleaning hard surfaces. According to Thomas Hedley & Co. Ltd. (now Procter & Gamble), British Patent 809,060 published Feb. 18, 1959, formula (I) compounds are useful as a surfactant for laundry detergents such as those having granular form. Hildreth (supra) mentions use of compounds of formula (I) in the biochemistry field as a detergent agent for solubilizing plasma membranes and EP-A 285,768, published Dec. 10, 1988 describes application of formula (I) compounds as a thickener. Thus, these compounds, or compositions containing them, can be highly desirable surfactants.

Yet another process for making compositions comprising formula (I) compounds is included in the above-identified disclosure of improved thickeners. See EP-A 285,768. See also H. Kelkenberg, Tenside Surfactants Detergents 25 (1988) 8–13, inter alia for additional disclosures of processes for making N-alkylglucamines which, along with the above-identified art-disclosed N-alkylglucamine processes can be combined with the instant process for an overall conversion of glucose and fatty materials to useful surfactant compositions.

The relevant disclosures of EP-A 285,768 include a brief statement to the effect that "it is known that the preparation of chemical compounds of formula (I) is done by reacting fatty acids or fatty acid esters in a melt with polyhydroxy alkylamines which can be N-substituted, optionally in the presence of alkaline catalysts". The above-referenced art strongly suggests that this statement is a gross simplification or is inaccurate.

EP-A 285,768 does not cite any references in support of the quoted statement, nor has any reference other than EP-A 285,768 been found which actually does disclose any catalytic condensation of N-alkylglucamines with fatty esters or fatty triglycerides.

The European Patent Application contains the following Example entitled "Preparation of N-methyl-coconut fatty acid glucamide" in which "Na methylate" is understood to be synonymous with "sodium methoxide" and which has been translated from the German:

"In a stirred flask 669 g (3.0 mol) of coconut fatty acid methyl ester and 585 g (3.0 mol) of N-methyl glucamine with the addition of 3.3 g Na methylate were gradually heated to 135° C. The methanol formed during the reaction was condensed under increasing vacuum at 100 to 15 mbar in a cooled collector. After the methanol evolution ended the reaction mixture was dissolved in 1.5 l of warm isopropanol, filtered and crystallized. After filtration and drying 882 g (=76% of theoretical) of waxy N-methyl coconut fatty acid glucamide was obtained. Softening point: =80° to 84° C.; Base number: 4 mg. KOH/g."

EP-A 285,768 continues with the following:

"In a similar manner the following fatty acid glucamides were prepared:

|  | Yield % | Softening Point (°C.) | Base No. (mg. KOH/g) |
| --- | --- | --- | --- |
| N-methyl lauric acid glucamide | 76 | 94–96 | 6 |
| N-methyl myristic acid glucamide | 75 | 98–100 | 3 |
| N-methyl palmitic acid glucamide | 75 | 103–105 | 5 |
| N-methyl stearic acid glucamide | 84 | 96–98 | 6" |

To summarize some important points of what can be gleaned from the art, the aforementioned Schwartz patent teaches that the problem of making formula (I) compounds from fatty esters or triglycerides and an N-alkylglucamine is solved by selecting fatty ester (instead of fatty acid) as the fatty reactant, and by doing simple uncatalyzed condensations. Later literature, such as Hildreth, changes direction back to a fatty acid-type synthesis, but does not document either that the teaching of the Schwartz patent is in error or how, short of making highly pure formula (I) compounds, to make such surfactants to detergent formulator's specifications. On the other hand, there has been one disclosure, in a totally different technical field, of sodium methoxidecatalyzed formula (I) compound synthesis. As noted, the procedure involves gradual temperature staging up to 135° C. and recrystallizing the product.

In view of the foregoing observations, it would be very desirable to further improve processes for making surfactant compositions comprising formula (I) compounds. Such processes should be useful on a large scale and should result directly in compositions meeting laundry detergent formulators' specifications without need for recrystallization.

Accordingly, it is an object of the instant invention to provide an improved catalyzed process for manufacturing surfactant compositions by reacting fatty esters and N-alkylglucamines in the presence of particular catalysts.

It is a further object to provide product compositions of the invention for use in laundry detergents, including not only linear glucamide surfactant compositions having excellent quality and color, but also compositions comprising the linear glucamide surfactant in combination with one or more solid-form alkaline laundry detergent builders such as sodium carbonate.

These and other objects are secured, as will be seen from the following disclosure.

SUMMARY OF THE INVENTION

The present invention relates to an improved process for preparing detergent surfactants, more specifically, surfactant compositions having a high proportion of compounds of formula (I) wherein R' is fatty alkyl and R is a short-chain hydrocarbyl, typically methyl, ethyl or the like. Products of the invention include the detergent surfactant, as well as detergent compositions consisting essentially of mixtures of the surfactant with one or more additional laundry-useful components, especially alkaline laundry detergent builders.

In general, the process involves reacting fatty esters and N-alkylglucamines in the presence of particular catalysts.

Catalysts suitable for use herein are selected from the group consisting of trilithium phosphate, trisodium phosphate, tripotassium phosphate, tetrasodium pyrophosphate, tetrapotassium pyrophosphate, pentasodium tripolyphosphate, pentapotassium tripolyphosphate, lithium hydroxide, sodium hydroxide, potassium hydroxide, calcium hydroxide, lithium carbonate, sodium carbonate, potassium carbonate, disodium tartrate, dipotassium tartrate, sodium potassium tartrate, trisodium citrate, tripotassium citrate, sodium basic silicates, potassium basic silicates, sodium basic aluminosilicates, potassium basic aluminosilicates and mixtures thereof.

Especially preferred catalysts include sodium carbonate and potassium carbonate.

The process efficiently converts the N-alkylglucamine, e.g., N-methyl-D-glucamine, to linear glucamide surfactant of quality suitable for the laundry detergent formulator, without need for recrystallization.

In a preferred embodiment, the invention encompasses a process wherein the catalyst is selected from the group consisting of sodium carbonate, potassium carbonate and mixtures thereof, the amount of said catalyst is from about 0.5 mole % to about 50 mole % on N-alkylglucamine, conversion of N-alkylglucamine to compounds having linear structure of formula

wherein R is the alkyl residue of the glucamine and R' is the residue of the fatty ester is about 70 mole % or higher on N-alkylglucamine, and conversion of N-alkylglucamine to cyclic glucamide or esteramide by-products is about 15 mole % or lower.

The present catalysts, as they operate in the process, have the advantage of not catalytically increasing the formation of by-product such as esteramide or cyclized glucamide at the same time as catalyzing the desired amidation reaction. This is surprising since esteramide by-product formation is an esterification reaction, and catalysts such as sodium carbonate or potassium carbonate have heretofore been used for catalyzing esterification reactions. See, for example, U.S. Pat. No. 2,999,858, Curtis, issued Sep. 12, 1961, which discloses a conversion of sucrose to sucrose fatty esters. See also U.S. Pat. 3,558,597, von Brachel et al, issued Jan. 26, 1971.

In short, the present invention is surprising in its ability to catalytically form surfactant compositions rich in formula (I) compounds selectively, without at the same time catalytically increasing by-product formation, especially by esterification.

In general, the present process takes N-alkylglucamines to linear glucamides of formula (I) with a conversion of about 70 mole % or higher, more preferably 80 mole % or higher based on N-alkylglucamine, whereas the conversion of N-alkylglucamine to by-product having cyclic glucamide or esteramide structure is generally about 15 mole % or lower.

The N-alkylglucamine starting-material can be prepared by any of the above-referenced literature methods and is illustrated by N-methylglucamine, N-ethylglucamine, N-propylglucamine and N-butylglucamine.

Highly preferred fatty ester is selected from saturated fatty methyl esters and fatty triglycerides.

The N-alkylglucamine and fatty ester are preferably used in approximately equimolar proportions in terms of the number of moles of fatty carbonyl moieties of the fatty ester per mole of N-alkylglucamine. Excellent results can also be achieved when there is a slight excess of fatty ester, e.g., about 1.05 to about 1.10 moles per mole of N-alkylglucamine.

The present invention has many advantages including a generally rapid and efficient process achieving a product which is useful without further purification for formulation in laundry detergents. The product of the process generally has good color and only low levels of nonvolatile by-product (notably cyclic by-product but also esteramides and the like). In certain embodiments of the invention, novel and useful compositions such as surfactant/builder intermediates for the formulator of granular laundry detergents are also secured.

Percentages and proportions herein are normally designated on a mole percentage basis unless otherwise indicated.

DETAILED DESCRIPTION OF THE INVENTION

The present invention relates to an improved catalyzed process for manufacturing linear glucamide surfactants from fatty esters and N-alkylglucamines. In the preferred product compositions, a high proportion (typically 70 mole % or higher, preferably 80 mole % or higher) of the N-alkylglucamine is converted to formula (I) compounds wherein R' is fatty alkyl and R is a short-chain hydrocarbyl, typically methyl, ethyl or the like.

When referring to "conversion" percentages herein, such conversion percentages are expressed on a mole percentage basis.

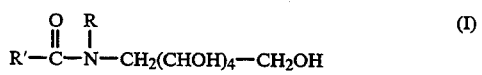

Although it is recognized that substantially pure compounds of formula (I) or, at the other extreme, highly impure compositions comprising (I) are not new, the term "linear glucamide surfactant" will be used herein to refer to the characteristic product of the process which is directly useful as a surfactant for large-scale laundry detergent formulation.

In general, "linear glucamide surfactant" as produced herein has a major proportion of the N-alkylglucamine starting-material converted to formula (I) compounds, while only minor proportions, e.g., 15 mole % or less, are converted to cyclic glucamide and/or esteramide.

By comparison, art-taught products such as those of Schwartz are believed to involve important conversion of the starting-material (e.g., 25 mole % or higher) to compounds departing from formula (I) by virtue of cyclization of the polyhydroxy moiety (cyclic glucamide) or esterification of the hydroxy moieties (esteramide).

In outline, the instant process comprises reacting a mixture of an N-alkylglucamine, a fatty ester and a catalyst.

Catalyst

Catalyst suitable for this invention is selected from the group consisting of trilithium phosphate, trisodium phosphate, tripotassium phosphate, tetrasodium pyrophosphate, tetrapotassium pyrophosphate, pentasodium tripolyphosphate, pentapotassium tripolyphosphate, lithium hydroxide, sodium hydroxide, potassium hydroxide, calcium hydroxide, lithium carbonate, sodium carbonate, potassium carbonate, disodium tartrate, dipotassium tartrate, sodium potassium tartrate, trisodium citrate, tripotassium citrate, sodium basic silicates, potassium basic silicates, sodium basic aluminosilicates, potassium basic aluminosilicates and mixtures thereof.

Preferred catalyst suitable for this invention is selected from the group consisting of trisodium phosphate, tripotassium phosphate, sodium hydroxide, potassium hydroxide, calcium hydroxide, sodium carbonate, potassium carbonate and mixtures thereof. The most highly preferred catalysts from this group are selected from sodium carbonate, potassium carbonate, sodium hydroxide, potassium hydroxide, and mixtures thereof.

Suitable aluminosilicates are better illustrated by the zeolites, especially Zeolite Na-A. Such siliceous catalysts are all preferably small size, such as from about 1-10 micron.

More generally, "catalyst" in the context of the present invention refers to a compound or mixture which significantly enhances the rate of formation of formula (I) compounds from N-alkylglucamine and fatty ester. This is a unique amidation reaction, since there are also present potentially reactive esterfiable or cyclizable hydroxyl groups in the N-alkylglucamine. More specifically still, the enhancement achieved by the catalyst includes at the lower end of the preferred temperatures of the process, forming the desired formula (I) compounds more rapidly than would otherwise be possible, and at the higher end of the preferred temperatures of the process, forming (I) extremely quickly, e.g., within a matter of a few minutes. Catalysts herein assist amidation without concurrently catalyzing unwanted side-reactions, such as cyclization and esteramide formation, to any appreciable extent under the reaction conditions: that is to say, the catalysts are selective.

The catalysts differ from any impurity compounds, such as water, soap or fatty acid, which might be inherent in the process when it is carried out using industrial grades of the primary reactants. Thus "catalyst" always refers to essential materials for the present process, which need to be added to the N-alkylglucamine and fatty ester for the invention to operate.

"Catalyst" is defined in a practical manner as referring to complete, stable chemical substances or mixtures thereof. The individual catalyst compounds or mixtures are available in commerce or can be made by literature methods. They can be weighed out and added to the other reactants in the instant process. Thus, catalysts herein are not defined as "active species" in the style of mechanistic discussions by chemists. Such species might or might not actually be generated in-situ in the reaction mixtures of the instant process. The invention is not to be considered limited by any such theory of catalyst operation.

Catalysts herein are generally compatible with the process. They do not contain highly reactive, grossly unsatisfactory functional groups such as peroxy, chloro, iodo, ketene, and so forth of the sort which ordinarily skilled chemists will generally recognize as not desirable for any elevated temperature amidation reactions of the present kind.

Catalysts herein preferably have particulate form: typically, they take the form of powders, as are generally available in commerce. Finely divided powders are generally preferred. Small particle sizes, such as a size of less than 50 micron or 1–10 micron can be very useful.

Catalysts herein preferably have substantially anhydrous form; hydrated salts may be usable but are significantly less preferred than anhydrous catalyst; aqueous catalyst solutions are excluded unless water is removed as further illustrated in the context of hydroxide catalysts hereinafter. Admission of water would lead to formation of fatty acids which are preferably minimized herein.

Highly preferred catalysts herein generally are water-soluble catalysts having monovalent cations: such preferred catalysts are more particularly illustrated by lithium carbonate, sodium carbonate and potassium carbonate.

Although alkali metal hydroxide catalysts are quite usable, they are not as preferred, at least on grounds of relatively difficult handling, as compared with the carbonates. A preferred sequence of steps when handling hydroxide catalyst comprises impregnating the N-alkylglucamine with an aqueous solution or methanolic solution, preferably an aqueous solution, of the hydroxide catalyst. In more detail, one such method for using sodium hydroxide or potassium hydroxide as catalysts in the instant process comprises adding the hydroxide as an aqueous solution to the N-alkylglucamine, typically at room temperature; drying the resulting intimate mixture of N-alkylglucamine and hydroxide catalyst under mild conditions, e.g., at 50° C. under vacuum, then reacting the dried intimate mixture with the fatty ester.

In general, the levels of catalyst used in the instant process are of about 0.5 mole % or higher, e.g., from about 0.5 mole % to about 50 mole % based on N-alkylglucamine. Preferred levels are from about 1 mole % to about 20 mole %, even more preferably from about 2 mole % to about 10 mole %.

In one highly preferred embodiment of the instant process, the catalyst is anhydrous potassium carbonate powder, at a level of from about 2 mole % to about 5 mole % on N-alkylglucamine.

Mixed catalysts are also useful herein, as illustrated by mixtures of sodium carbonate and potassium carbonate in varying proportions.

Particularly useful as catalyst herein is porous granular anhydrous potassium carbonate, though porosity is not essential when the catalyst takes the form of a fine powder.

It will immediately be apparent that the instant process is remarkable in identifying much milder and more convenient catalysts than sodium methoxide for improved linear glucamide surfactant formation.

N-alkylglucamine

Various N-alkylglucamines are useful in the practice of this invention. Such N-alkylglucamines are more specifically illustrated by N-methylglucamine, N-ethylglucamine, N-propylglucamine and N-butylglucamine. The preferred N-alkylglucamines are derived from D-glucose, e.g., N-methyl-D-glucamine.

The N-alkylglucamine can be pure or can be industrial grade provided that certain specifications are adhered to. Thus, industrial grade N-alkylglucamine may contain sugars such as glucose, sorbitol or other relatively inert by-products from N-alkylglucamine manufacture (typically 0–5 weight %). However, industrial grade N-alkylglucamines for this process should have low or negligibly small contents, in parts per million, (e.g., 0–20 ppm, preferably 0–2 ppm) of transition metals such as nickel if the formation of color bodies or other adverse effects are to be minimized. It has been found that industrial grade N-alkylglucamines commonly contain such transition metals as a result of their manufacture by transition metal- catalyzed reductive animation of glucose or corn syrup.

The N-alkylglucamines used herein are generally of good color, preferably pure white with no trace of colored impurities. Also, the N-alkylglucamine is preferably substantially anhydrous.

One convenient check for N-alkylglucamine quality involves simply heating a sample to the temperature of the present process, e.g., 140° C. Industrial grade N-alkylglucamines which quickly darken at such a temperature are very likely to contain unacceptable levels of impurity.

It is usually possible to clean up industrial grade N-alkylglucamines which fail initial quality checks, either by washing them with methanol/water or by recrystallizing them. A useful method for lowering the level of nickel is to filter a solution of the N-alkylglucamine through basic silica gel or bleaching earth.

Fatty Ester

The fatty ester used herein is preferably a fatty (e.g., $C_{12}$–$C_{20}$) methyl ester or triglyceride which is highly saturated, although other esters, such as saturated and mixed saturated/unsaturated fatty ethyl esters, fatty monoglycerides or fatty diglycerides can also be used. Suitable fatty esters include those illustrated by Schwartz, supra. Preferred fatty esters are better illustrated by lauric methyl ester, palmitic methyl ester or, if a mixture of chain lengths is used, coconut methyl ester. When industrial grade fatty esters are used, excellent results are achieved with the following:

| Procter & Gamble CE-1270 Methyl Ester: | |
| --- | --- |
| Acid Value: | 0.2 |
| Iodine Value: | 0 |
| Moisture (%, K · F) | 0.03 |
| Color (% transmittance at 460 nm) | 97 |
| Chain Length (GC, Wt %) | |
| C 10 | 0.4 |
| C 12 | 73.0 |
| C 14 | 25.9 |
| C 16 | 0.2 |
| Procter & Gamble CE-1218 Methyl Ester: | |
| Acid Value: | 0.6 |
| Saponification Value | 242 |
| Iodine Value: | 9.4 |

| -continued | |
| --- | --- |
| Moisture (%, K · F) | 0.04 |
| Color (% transmittance at 460 nm) | 97 |
| Chain Length (GC, Wt %) | |
| C 10 | 0.5 |
| C 12 | 57.4 |
| C 14 | 20.7 |
| C 16 | 10.0 |
| C 18 | 1.9 |
| C 18 1-unsaturated | 7.3 |
| C 18 2-unsaturated | 1.5 |
| C 20 | 0 |

Substantially pure lauric methyl ester and palmitic methyl ester can of course also be used. Preferred industrial grade fatty ester for use in the present process typically contains 10 ppm or lower, better 0 ppm of heavy metals, and a free fatty acid content of 5 weight % or lower, preferably 1 weight % or lower.

The N-alkylglucamine and fatty ester mix with some difficulty in the present process. This is especially true when the fatty esters are relatively hydrophobic, e.g., the ethyl esters of $C_{16}$ saturated fatty acids as compared with coconut methyl esters. With the most hydrophobic fatty esters such as $C_{16}$ or higher ethyl esters or triglycerides, satisfactory reaction can be very difficult. To solve this problem, it has been discovered that nonionic surfactants such as a preformed formula (I) compound wherein R' is $C_{11}H_{23}$ and R is methyl may be used as a phase transfer agent or emulsifier. When a phase transfer agent is used in the instant process, it is used at a level of from about 0.5% to about 95% by weight of the reaction mixture. High levels such as 50% or more are best reserved for continuous mode embodiments where reaction times can be kept very short. In a batch (i.e., noncontinuous) process, a preferred level is from about 0.5 weight to about 20 weight %, even more preferably from about 1 weight % to about 10 weight %. Such levels are also suitable for use in continuous mode embodiments.

Continuous mode embodiments will, of course, concurrently recycle some catalyst.

More generally, phase transfer agents herein comprise a member selected from the group consisting of nonionic surfactants. More preferably, the phase transfer agent consists essentially of a member selected from the group consisting of saturated fatty alcohol polyethoxylates, alkylpolyglycoside surfactants or the like.

Thus the present invention has preferred embodiments which introduce the notion of a carbonate-catalyzed, phase-transfer-assisted condensation of N-alkylglucamines and fatty esters to form surfactants of formula (I).

Reaction Conditions

In general, the temperatures, pressures, times and proportions of the two principal reactants can be as disclosed in the art. Temperatures in the present process are normally from about 120° C. to about 200° C., more preferably about 138° C. or higher. Reaction periods in the process are normally from about 0.5 minutes to about 5 hours.

The invention does, however, identify preferred temperatures and reaction periods depending on whether the process is carried out in a continuous mode or a non-continuous mode. Thus, in a noncontinuous mode a preferred temperature is from about 138° C. to about 170° C. and the corresponding period is from about 20 minutes to about 90 minutes. In a continuous mode, a preferred temperature is from about 160° C. to about 200° C. and a corresponding period is from about 0.5 minutes to about 10 minutes. Generally, higher temperatures are accompanied by the shorter times. Moreover, higher catalyst levels speed up the process so that shortest times are associated with the higher catalyst levels.

Referring to the art, Schwartz favors high temperatures such as those of the order of 170° C., one must assume because he did not have suitable catalysts: such temperatures, especially with relatively long reaction times, e.g., an hour or more, can significantly increase by-product formation, especially cyclization.

EP-A 285,768 has slow heating to relatively low temperatures, specifically 135° C.: this may be due to the need to avoid charring with the sodium methoxide catalyst, and is relatively uneconomic.

It is preferred to conduct the present process in the absence of air or oxygen. This is conveniently accomplished by maintaining an inert atmosphere of nitrogen or argon over the reaction mixtures, or by applying vacuum, the latter especially in the later stages of the process.

When operating uncatalyzed processes not in accordance with this invention, e.g., using the Schwartz process, at such moderate temperatures, very long reaction times (typically several hours) are required, rendering the uncatalyzed process at such temperatures rather unattractive due to long reactor hold-ups. For example, at about 150° C., the Schwartz process typically requires about 7–8 hours.

In contrast, when operating according to the present catalyzed and solventless process in the above-indicated preferred temperature ranges, e.g., at about 150° C. in a batch mode at a typical catalyst level of about 2 mole %, reaction times need be no more than 90 minutes. Continuous processing with much shorter reaction times is of course possible.

According to the present invention, it is highly preferred that the reaction should be checked for completion by any suitable technique, e.g., by watching for the end of methanol evolution, by thin layer chromatography (see hereinafter), or by gas chromatography, so that it can be stopped by cooling just as soon as it is complete.

The present process is generally carried out using stirring to mix the reactants properly. It should be appreciated that at the outset of the instant process, the reaction mixtures are three-phase, the phases comprising a liquid fatty ester phase, a molten N-alkylglucamine phase and a solid catalyst phase. Therefore it can be appreciated how important it is to properly mix the reactants. Best results are generally achieved in reactors designed for effective heat and mass transfer. The use of baffles in the reactor can be advantageous.

Relative proportions of N-alkylglucamine and fatty ester are generally as disclosed by Schwartz, U.S. Pat. No. 2,703,798, incorporated by reference. Typical proportions are approximately equimolar for best results.

Processes herein generally do not need, and are preferably conducted without added solvents and therefore generally differ from the art-disclosed process of Hildreth supra. The instant process is however tolerant of, and can even benefit from, the presence of varying amounts of methanol, ethanol, and glycerin, which are actually process by-products. Glycols such as ethylene glycol, 1,2-propylene glycol and glycerin can be added early in the process, typically in relatively small, non-solvent amounts, as activators.

Vacuum is optionally applied during the present process, particularly as the process goes toward completion, for efficient removal of volatiles (especially methanol) when generated in the process. Use of vacuum can also improve product odor. When the fatty ester is a triglyceride, glycerin is formed during the process instead of methanol. The glycerin does not have to be removed from product of the process in all cases, since it can be useful in the final product or derivative thereof (a typical example being a bar soap stamped out from product of the invention).

It is possible to use the catalyst both for its catalytic function and for other desirable functions, to have it as an integral part of the final product. Thus the process has advantages of manufacturing simplicity and is especially valuable when the catalyst is known to be useful for its laundry detergent function. What has not hitherto been appreciated is to use as catalysts for linear glucamide formation materials which can later function in the product to modify its desirable properties, such as the water-dispersability of linear glucamide-containing particles. Water-dispersibility can be modified, especially upwardly, when the catalyst or phase transfer agent is highly water-soluble or capable of lowering the Krafft boundary of the glucamide. This is highly desirable for manufacture of low-temperature or all-temperature detergents.

Accordingly the new approach of the present invention results in an economically attractive option for making unique granular detergent intermediates, such as particles containing intimate mixtures of linear glucamide surfactants with the catalytically active or phase transfer-active materials. Such particles are easily dispersed in water and offer increased manufacturing convenience to detergent formulators since they can be directly dry-mixed with other detergent ingredients rather than requiring additional premix process steps.

The simplicity of the present process makes it widely useful both nationally and abroad, e.g., in less sophisticated industrial economies.

The process of the invention has many alternate embodiments. Thus a number of addition sequences can be used. In one such sequence, a process is encompassed comprising the following ordered sequence of steps: (a) preheating the fatty ester to the above-identified temperatures; (b) adding the N-alkylglucamine at said temperature and mixing to the extent needed to form a two-phase liquid/liquid mixture; (c) mixing in the catalyst; and (d) stirring at said temperature until the end of the above-identified reaction period.

In yet another sequence, the following steps are carried out: (a) preheating a solid/liquid mixture of N-alkylglucamine and fatty ester to the above-identified temperatures with mixing, thereby melting the N-alkylglucamine and concurrently mixing it with the fatty ester in the shortest practical time; (b) at said temperatures, adding pre-formed product with stirring, said pre-formed product providing linear glucamide surfactant for phase transfer and concurrently providing a portion of the catalyst; the total amount of said pre-formed product added as combined phase transfer agent and catalyst being from about 2% to about 20% by weight of the reactants; (c) at said temperature, adding additional catalyst in an amount sufficient to attain the above-identified catalyst levels; and (d) continuing to react with stirring until the end of the reaction period.

To such a sequence can be added a step (e): mixing the product of step (d) in molten form with a large excess of said catalyst, thereby forming a linear glucamide surfactant/alkaline detergency builder mixture.

EXAMPLE I

Although a skilled chemist can vary apparatus configuration, one suitable apparatus for use herein comprises a three-liter four-necked flask fitted with a motor-driven paddle stirrer and a thermometer of length sufficient to contact the reaction medium. The other two necks of the flask are fitted with a nitrogen sweep and a wide-bore side-arm (caution: a wide-bore side-arm is important in case of very rapid methanol evolution) to which is connected an efficient collecting condenser and vacuum outlet. The latter is connected to a nitrogen bleed and vacuum gauge, then to an aspirator and a trap. A 500 watt heating mantle with a variable transformer temperature controller ("Variac") used to heat the reaction is so placed on a lab-jack that it may be readily raised or lowered to further control temperature of the reaction.

N-methylglucamine (195 g., 1.0 mole, Aldrich, M4700-0) and methyl laurate (Procter & Gamble CE 1270, 220.9 g, 1.0 mole) are placed in the flask. The solid/liquid mixture is heated with stirring under a nitrogen sweep to form a melt (approximately 25 minutes). When the melt temperature reaches 145° C., catalyst (anhydrous powdered sodium carbonate, 10.5 g., 0.1 mole, J. T. Baker) is added. The nitrogen sweep is shut off and the aspirator and nitrogen bleed are adjusted to give 5 inches (5/31 atm.) Hg. vacuum. From this point on, the reaction temperature is held at 150° C. by adjusting the Variac and/or by raising or lowering the mantle.

Within 7 minutes, first methanol bubbles are sighted at the meniscus of the reaction mixture. A vigorous reaction soon follows. Methanol is distilled over until its rate subsides. Then adjust vacuum to give about 10 inches Hg. (10/31 atm.) vacuum. The vacuum is increased approximately as follows (in inches Hg at minutes): 10 at 3, 20 at 7, 25 at 10. 11 minutes from the onset of methanol evolution, heating and stirring are discontinued co-incident with some foaming. Analysis by TLC (see after) shows that at this point, the process is complete. The product is cooled and solidifies.

EXAMPLE II

A baffled stainless steel jacketed reactor is provided. The reactor has a pressurizable steam-jacket and is equipped with a motor-driven stirrer, temperature measuring means, nitrogen/vacuum inlet/outlets similar to the arrangement in Example I, and a wide-bore side-arm connected to an efficient methanol collection condenser and trap. The reactor has a sight-glass closable port and a ball-valve closable port for reactant addition and can be drained through a third port at the base. Steam can be passed through the jacket at controllable pressures of up to 150 psi so that the reactor can quickly be heated to controlled temperatures up to 150° C. or higher.

Fatty methyl ester (41.5 lbs., 18.85 kg., 85.68 gram moles, Procter & Gamble CE-1270 Methyl Ester) is charged to the clean, nitrogen-purged reactor through the sight-glass port. The stirrer is set in motion and steam at 50 psi. is used to heat the stirred methyl ester to 100° C. (212° F.). Now N-methylglucamine (36.8 lbs, 16.71 kg., 85.68 gram moles, 99% + purity, heavy metal content <2 ppm, Aldrich or Merck) is added through the sight glass port. The ports are closed and the reactor is heated at ambient pressure under nitrogen with stirring using 70 psi. steam so that the temperature reaches 130° C. (266° F.) and substantially all the N-methylglucamine has dissolved or melted.

A partial vacuum of 46 cm Hg. is now applied.

Catalyst (potassium carbonate anhydrous powder (<50 microns, 236 grams, 1.71 gram mole, LCP Chemicals) is added under nitrogen through the ball valve port when the reactor internal temperature is about 138° C. (280° F.).

Reaction is continued by stirring and holding the vacuum in the range 40–60 cm Hg. for about 90 minutes, the vacuum being adjusted as needed to control foaming.

The steam pressure is released and the contents of the reactor are drained as a melt onto a flat steel surface where solidification can occur. After holding at about 20° C. for a period sufficient to allow embrittlement, e.g., 18 hours, the product is broken into flakes and is ground to a powder.

EXAMPLE III

The procedure of Example II is repeated, with the exception that the reaction time is about 30 minutes and the product is secured as a concentrated aqueous mixture by slow addition of water to the rapidly stirred product in the reactor, starting at temperatures just above the melting-point.

EXAMPLE IV

The procedure of Example II is repeated except that an equimolar amount of Procter & Gamble Methyl Ester CE-1295 is substituted for the CE-1270 Ester.

EXAMPLE V

The procedure of Example I is repeated except that the fatty methyl ester is substituted by an equimolar amount of coconut oil and about 40 grams of preformed product of Example I is added as a phase transfer agent.

EXAMPLE VI

The procedure of Example I is repeated except that the molten product is poured onto 1000 grams of sodium carbonate anhydrous powder preheated to 150° C. and thoroughly mixed with a cake-beater while slowly cooling to about 25° C. The product is a granule which is useful as an intermediate for formulating granular laundry detergents. It can also be used directly for washing fabrics in an aqueous laundry bath, with excellent results.

EXAMPLE VII

The procedure of Example I is repeated except that about 40 grams of substantially pure $CH_3(CH_2)_{10}C(O)N(CH_3)CH_2(CHOH)_4CH_2OH$, as a phase transfer agent, is added to the mixture of molten N-methylglucamine and Procter & Gamble CE 1270 methyl ester.

Thin Layer Chromatography (TLC) Analysis

Processes herein can be monitored by TLC using Silica Gel GF plates (Analtech) and a solvent system consisting of $CHCl_3$: $MeOH$:$NH_4OH$ at a volume ratio of 80:23:3. Plates are preconditioned in 2:1 v/v $CHCl_3$:MeOH prior to use to eliminate discoloration at the solvent front.

A typical procedure for analysis involves preparing in methanol a 5-10 wt. % solution of a sample from the process. The plates are spotted with the solution, dried, and processed in the 80:23:3 solvent solution for about 10-15 minutes. Plates are removed from the processing chamber and heat-dried. Upon cooling, the plates are dipped in a 10 wt. % solution of phosphomolybdic acid and allowed to dry. The plates are then placed on hotplate at moderate heat for 5-10 minutes until the spots are pronounced. Overheating can cause discoloration of plate and fading of spots. An iodine chamber treatment can be used instead of the phosphomolybdic acid dip but staining is less permanent. Typical RF factors are:

| COMPOUND | RF |
|---|---|
| Unreacted N-methyl-D-glucamine | 0.0 |
| Fatty acid impurity | 0.2 |
| Formula (I) compound | 0.3 |
| Cyclic by-product from dehydration of formula (I) compound | 0.5 |
| Esteramide by-product | 0.7 |
| Unreacted fatty ester | 0.9 |

What is claimed is:

1. In a process for preparing a linear glucamide surfactant of the formula

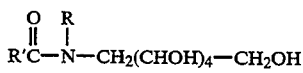

from the reaction of a fatty acid ester and an N-alkylglucamine which is a member selected from the group consisting of N-methylglucamine, N-ethylglucamine, N-propylglucamine and N-butylglucamine, wherein R is the alkyl residue of said N-alkylglucamine and R' is the residue of the fatty acid eter, the improvement which comprises conducting said reaction using an N-alkylglucamine having a heavy metal content of about 20 ppm or lower and a free sugar content of about 5 weight percent or lower in the presence of from about 2 mole percent to about 10 mole percent, based on N-alkylglucamine, of a catalyst which is a member selected from the group consisting of trilithium phosphate, trisodium phosphate, tripotassium phosphate, tetrasodium pyrophosphate, tetrapotassium pyrophosphate, pentasodium tripolyphosphate, pentapotassium tripolyphosphate, lithium hydroxide, sodium hydroxide, potassium hydroxide, calcium hydroxide, lithium carbonate, sodium carbonate, potassium carbonate, disodium tartrate, dipotassium tartrate, sodium potassium tartrate, trisodium citrate, tripotassium citrate, sodium basic silicates, potassium basic silicates, sodium basic aluminosilicates, potassium basic aluminosilicates and mixtures thereof, whereby the conversion of N-alkylglucamine to glucamine surfactant is about 80 mole percent or higher and the conversion of N-alkylglucamine to cyclic glucamide or esteramide by-products is about 10 mole percent or lower.

2. A process according to claim 1 wherein said N-alkylglucamine, fatty ester and catalyst are reacted as a mixture at a temperature of from about 138° C. to about 170° C. for a period of from about 20 minutes to about 90 minutes.

3. A process according to claim 1 wherein said N-alkylglucamine, fatty ester and catalyst are reacted as a mixture at a temperature of from about 160° C. to about 200° C. for a period of from about 0.5 minutes to about 10 minutes.

* * * * *